(12) United States Patent
Shin

(10) Patent No.: US 10,787,426 B2
(45) Date of Patent: Sep. 29, 2020

(54) METHOD OF TREATING AUTISM SPECTRUM DISORDERS USING PIPERAZINE-1-CARBOXAMIDINE OR PHARMACEUTICALLY ACCEPTABLE SALT THEREOF

(71) Applicant: NEUROVENTI, Seoul (KR)

(72) Inventor: Chan Young Shin, Seoul (KR)

(73) Assignee: NEUROVENTI, Seoul (KR)

( * ) Notice: Subject to any disclaimer, the term of this patent is extended or adjusted under 35 U.S.C. 154(b) by 44 days.

(21) Appl. No.: 16/300,298

(22) PCT Filed: May 10, 2017

(86) PCT No.: PCT/KR2017/004826
§ 371 (c)(1),
(2) Date: Mar. 18, 2019

(87) PCT Pub. No.: WO2017/196078
PCT Pub. Date: Nov. 16, 2017

(65) Prior Publication Data
US 2019/0202796 A1   Jul. 4, 2019

(30) Foreign Application Priority Data
May 10, 2016   (KR) .................. 10-2016-0057095

(51) Int. Cl.
| *A61K 31/495* | (2006.01) |
| *C07D 295/13* | (2006.01) |
| *A61K 9/00* | (2006.01) |
| *A61P 25/00* | (2006.01) |
| *A61P 25/08* | (2006.01) |
| *A23L 33/10* | (2016.01) |

(52) U.S. Cl.
CPC .......... *C07D 295/13* (2013.01); *A61K 9/0019* (2013.01); *A61K 9/0053* (2013.01); *A61K 31/495* (2013.01); *A61P 25/00* (2018.01); *A61P 25/08* (2018.01); *A23L 33/10* (2016.08); *A23V 2002/00* (2013.01)

(58) Field of Classification Search
CPC .................................... A61K 31/495
USPC .................................... 514/252.12
See application file for complete search history.

(56) References Cited

FOREIGN PATENT DOCUMENTS

| KR | 2016-0057095 | 7/1917 |
| KR | 10-2012-0081119 | 7/2012 |
| KR | 10-1288781 | 7/2013 |
| WO | WO 03-053942 | 7/2003 |

OTHER PUBLICATIONS

Piletz et al., "Putative Agmatinase Inhibitor for Hypoxic-Ischemic New Born Brain Damage", Neurotox. Res., 2013, vol. 24, No. 2, pp. 176-190 (Year: 2013).*
Reichow and Volkmar, "Narrowing of 'autism' in DSM-5 runs counter to idea of broad spectrum", Spectrum, 2018, https://www.spectrumnews.org/opinion/viewpoint/narrowing-autism-dsm-5-runs-counter-idea-broad-spectrum/ (Year: 2018).*
Centers for Disease Control and Prevention, "Signs and Symptoms of Autism Spectrum Disorders", https://www.cdc.gov/ncbddd/autism/signs.html (accessed Oct. 28, 2019) (Year: 2019).*
Centers for Disease Control and Prevention, "Treatment for Autism Spectrum Disorder", https://www.cdc.gov/ncbddd/autism/treatment.html (accessed Oct. 28, 2019) (Year: 2019).*
Piletz et al., "Putative Agmatinase Inhibitor for Hypoxic-Ischemic New Born Brain Damage", Neurotox Res, 2013, vol. 24, pp. 176-190 (Year: 2013).*
Browning, et al., "Electroshock- and Pentylenetetrazol-Induced Seizures in Genetically Epilepsy-Prone Rats (GEPRs): Differences in Threshold and Pattern," *Epilepsy Research*, 6(1); 1-11, 1990.
Crawley, "Designing Mouse Behavioral Tasks Relevant to Autistic-Like Behaviors," *Mental Retardation and Developmental Disabilities Research Reviews*, 10(4); 248-258, 2004.
International Search Report Issued in Corresponding PCT Application No. PCT/KR2017/004826, dated Sep. 14, 2017.
Kim, et al., "Prevalence of Autism Spectrum Disorders in a Total Population Sample," *American Journal of Psychiatry*, 168(9); 904-12; 2011.
Kim, et al., "Subchronic Treatment of Donepezil Rescues Impaired Social, Hyperactive, and Stereotypic Behavior in Valproic Acid-Induced Animal Model of Autism," *PloS One*, 9(8);e104927, 2014.
Kim, et al., Agmatine Rescues Autistic Behaviors in the Valproic Acid-Induced Animal Model of Autism, *Neuropharmacology*, 113; 71-81, 2017.
Lai, et al., "Autism," *Lancet*, 383(9920); 896-910, 2014.
McFarlane, et al., "Autism-Like Behavioral Phenotypes in BTBR T+tf/J Mice," *Genes, Brain and Behavior*, 7(2); 152-163, 2008.
Park, et al., "Anticonvulsant Effect of Wogonin Isolated from Scrutellaria Baicalensis," *European Journal of Pharmacology*, 574. 2,; 112-119, 2007.
Piletz, et al., "Putative Agmatinase Inhibitor for Hypoxic-Ischemic New Born Brain Damage," *Neurotoxicity Research*, 24; 176-190, 2013.

\* cited by examiner

*Primary Examiner* — Raymond J Henley, III
(74) *Attorney, Agent, or Firm* — Norton Rose Fulbright US LLP

(57) ABSTRACT

The present invention relates to a pharmaceutical composition for preventing or treating autism spectrum disorder, which includes piperazine-1-carboxamidine or a pharmaceutically acceptable salt thereof as an active ingredient. In particular, the piperazine-1-carboxamidine of the present invention exhibits, in valproic acid-induced autism rat models, an effect of improving the degrees of social interaction and social preference, reducing repetitive or restricted behaviors, hyperactivity, and impulsive behaviors, and also enhancing electroshock-induced seizure threshold susceptibility, and thus the piperazine-1-carboxamidine of the present invention may be used as an active ingredient of a pharmaceutical composition for preventing or treating direct causative symptoms, such as hyperactivity, lack of sociability, and epileptic convulsions of autism spectrum disorder.

6 Claims, 6 Drawing Sheets

METHOD OF TREATING AUTISM SPECTRUM DISORDERS USING PIPERAZINE-1-CARBOXAMIDINE OR PHARMACEUTICALLY ACCEPTABLE SALT THEREOF

CROSS-REFERENCE TO RELATED APPLICATIONS

This application is a national phase application under 35 U.S.C. § 371 of International Application No. PCT/KR2017/004826, filed May 10, 2017, which claims priority to and the benefit of Korean Patent Application No. 10-2016-0057095, filed on May 10, 2016, the disclosures of which are incorporated herein by reference in their entirety.

FIELD OF THE DISCLOSURE

The present invention relates to a pharmaceutical composition for preventing or treating autism spectrum disorder, which includes piperazine-1-carboxamidine or a pharmaceutically acceptable salt thereof as an active ingredient.

BACKGROUND ART

Autism spectrum disorder (ASD) refers to a range of neurodevelopmental disorders that are characterized by major symptoms such as a restricted range of behaviors and interests, a verbal or non-verbal communication disorder, reduced understanding of social interactions, or the like. It was referred to as autism in the past, but the diagnosis name has recently been revised to autism spectrum disorder to emphasize that the severity of autism and the prognosis thereof are very diverse. Autism spectrum disorder (ASD) includes autism, Asperger's syndrome, Rett's disorder, childhood disintegrative disorder, and pervasive developmental disorders (PDD) including pervasive developmental disorder not otherwise specified (PDD NOS) and the like.

Autism spectrum disorder appears before the age of three as developmental delay or abnormal functions in at least one area from among qualitative defects in social interactions, qualitative defects in communication, hyperactivity, and restricted repetitive behaviors, and are accompanied by symptoms such as intellectual disability, sleep disorders, gastrointestinal problems, epilepsy, or impulsive behaviors other than main symptoms.

The incidence of autism spectrum disorder is about one per 100 people worldwide, and is about 1 per 68 people in the United States according to a 2012 report of the Centers for Disease Control (Lai M C, Lombardo M V, Baron-Cohen S (2014). Autism. *Lancet* 383(9920): 896-910). In Korea, a governmental survey has never been conducted, but according to epidemiological studies for children living in the Ilsan region, it is reported that 2.64% of children aged between 7 years and 12 years has autism or other forms of autism spectrum disorder (Kim, Young Shin, et al. American Journal of Psychiatry, 2011).

As the prevalence of autism spectrum disorder increases every year, awareness of the risk of autism has been raised, and thus studies on analyzing a causative mechanism for autism spectrum disorder continue to be conducted. Accordingly, approximately 700 genes and factors such as exposure to valproic acid, thalidomide, and the like after pregnancy, the age of parents, or the like are known, but it is assumed that various genetic and environmental factors are involved in pathogenic mechanisms independently or interrelatedly, and pathophysiological causes and mechanisms of autism have not yet been found.

Thus, a method of diagnosing autism spectrum disorder through molecular biological or pathological indicators has not yet been established, there are no therapeutic agents for the causes, and only symptomatic drug treatment for accompanying symptoms such as epilepsy, self-injury, aggressive behavior, anxiety, emotional disturbances, and the like is conducted, but there are no therapeutic agents capable of treating the lack of sociability and repetitive behaviors, which are core symptoms. Rudimentary research on treatment responses to existing psychiatric drugs such as fluoxetine, clozapine, and the like as experimental drugs is ongoing, and although there are experimental drugs such as D-cycloserine, oxytocin, Methallothionein I/II, Gold, and the like, systematic efficacy studies have never been reported.

Therefore, the inventors of the present invention made efforts to develop a drug capable of exhibiting a direct therapeutic effect on major symptoms of autism spectrum disorder, and consequently verified that piperazine-1-carboxamidine (PZC) had, in valproic acid-induced autism rat models, an effect of improving the degrees of social interaction and social preference, reducing repetitive or restricted behaviors, hyperactivity, and impulsive behaviors, and also enhancing electroshock-induced seizure threshold susceptibility, and thus the piperazine-1-carboxamidine of the present invention could be used as an active ingredient of a pharmaceutical composition for preventing or treating autism spectrum disorder, thus completing the present invention.

SUMMARY OF THE INVENTION

Therefore, the inventors of the present invention verified that piperazine-1-carboxamidine (PZC) had an effect of treating and alleviating hyperactivity, lack of sociability, and epileptic convulsions in autism rat models, thus completing the present invention based on this finding.

Therefore, an object of the present invention is to provide a pharmaceutical composition for preventing or treating autism spectrum disorder.

In addition, another object of the present invention is to provide a health functional food for preventing or treating autism spectrum disorder.

According to an aspect of the present invention, there is provided a pharmaceutical composition for preventing or treating autism spectrum disorder, including a derivative represented by Formula 1 below or a pharmaceutically acceptable salt thereof as an active ingredient:

[Formula 1]

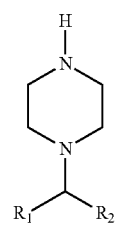

wherein, in Formula 1, each of $R_1$ and $R_2$ is independently O, H, a $C_1$-$C_4$ alkyl, a $C_1$-$C_4$ carboxyl group, or a double-bonded primary amine (=NH) or a single-bonded secondary amine ($NH_2$).

In an exemplary embodiment of the present invention, the derivative may be piperazine-1-carboxamidine represented by Formula 2 below:

[Formula 2]

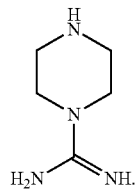

In an exemplary embodiment of the present invention, the autism spectrum disorder may be any one or more symptoms selected from the group consisting of hyperactivity, lack of sociability, and epileptic convulsions.

The present invention also provides a health functional food for preventing or treating autism spectrum disorder, including a derivative represented by Formula 1 below or a pharmaceutically acceptable salt thereof as an active ingredient:

[Formula 1]

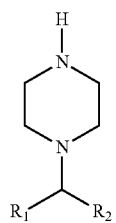

wherein, in Formula 1, each of $R_1$ and $R_2$ is independently O, H, a $C_1$-$C_4$ alkyl, a $C_1$-$C_4$ carboxyl group, or a double-bonded primary amine (=NH) or a single-bonded secondary amine ($NH_2$).

The present invention also provides a method of preventing or treating any one or more symptoms selected from the group consisting of hyperactivity, lack of sociability, and epileptic convulsions, the method including administering an effective amount of the derivative of Formula 1 or a pharmaceutically acceptable salt thereof to an individual with autism spectrum disorder.

The present invention also provides a use of the derivative represented by Formula 1 or a pharmaceutically acceptable salt thereof in a pharmaceutical composition for the prevention or treatment of any one or more symptoms selected from the group consisting of hyperactivity, lack of sociability, and epileptic convulsions, which appear in autism spectrum disorder.

The present invention also provides a use of the derivative represented by Formula 1 or a pharmaceutically acceptable salt thereof in a health functional food for the prevention or treatment of any one or more symptoms selected from the group consisting of hyperactivity, lack of sociability, and epileptic convulsions, which appear in autism spectrum disorder.

The present invention also provides a method of preventing or treating any one or more symptoms selected from the group consisting of hyperactivity, lack of sociability, and epileptic convulsions, the method including administering an effective amount of the piperazine-1-carboxamidine represented by Formula 2 to an individual with autism spectrum disorder.

The present invention also provides a use of the piperazine-1-carboxamidine represented by Formula 2 in a pharmaceutical composition for the prevention or treatment of any one or more symptoms selected from the group consisting of hyperactivity, lack of sociability, and epileptic convulsions, which appear in autism spectrum disorder.

The present invention also provides a use of the piperazine-1-carboxamidine represented by Formula 2 in a health functional food for the prevention or treatment of any one or more symptoms selected from the group consisting of hyperactivity, lack of sociability, and epileptic convulsions, which appear in autism spectrum disorder.

Therefore, the present invention provides a pharmaceutical composition for preventing or treating autism spectrum disorder, which includes piperazine-1-carboxamidine (PZC) as an active ingredient.

The piperazine-1-carboxamidine of the present invention exhibits, in valproic acid-induced autism rat models, an effect of improving the degrees of social interaction and social preference, reducing repetitive or restricted behaviors, hyperactivity, and impulsive behaviors, and also enhancing electroshock-induced seizure threshold susceptibility, and thus the piperazine-1-carboxamidine of the present invention can be used as an active ingredient of a pharmaceutical composition for preventing or treating direct causative symptoms, such as hyperactivity, lack of sociability, and epileptic convulsions of autism spectrum disorder.

BRIEF DESCRIPTION OF DRAWINGS

FIGS. 2A and 2B illustrates results of confirming a sociability enhancement effect of piperazine-1-carboxamidine on autism spectrum disorder, wherein FIG. 2A illustrates a sociability enhancement effect obtained by piperazine-1-carboxamidine in autism rat models; and FIG. 2B illustrates a social preference enhancement effect obtained by piperazine-1-carboxamidine in the autism rat models.

FIGS. 4A and 4B illustrates hyperactivity and impulsive behavior enhancement effects of piperazine-1-carboxamidine on autism spectrum disorder, wherein FIG. 4A illustrates an effect of piperazine-1-carboxamidine on reducing hyperactivity in autism rat models, and FIG. 4B illustrates an effect of piperazine-1-carboxamidine on alleviating impulsive disorders in autism rat models.

DETAILED DESCRIPTION OF THE INVENTION

As described above, autism spectrum disorder appears as major symptoms such as hyperactivity, lack of sociability, and the like, and is accompanied by epileptic convulsions and the like, but there has been no report about a drug for preventing and treating such major symptoms of autism spectrum disorder.

Piperazine-1-carboxamidine according to the present invention exhibits a therapeutic effect against direct or indirect symptoms such as hyperactivity, lack of sociability, and epileptic convulsions of autism spectrum disorder, and thus may be usefully used as an active ingredient of a pharmaceutical composition for the prevention or treatment of autism spectrum disorder.

The term "prevention" as used herein means all actions that inhibit or delay the onset of diseases via administration of the composition.

The term "alleviation" or "treatment" as used herein means all actions that alleviate or beneficially change symptoms due to the diseases via administration of the composition.

The term "administration" as used herein means providing a patient with a predetermined substance by using an appropriate method, and the composition of the present invention may be orally or parenterally administered via all general routes as long as they allow the composition to reach target tissues. In addition, the composition may be administered using an arbitrary device capable of delivering an active material of the composition to target cells.

Therefore, the present invention provides a pharmaceutical composition for preventing or treating autism spectrum disorder, which includes a derivative represented by Formula 1 below or a pharmaceutically acceptable salt thereof as an active ingredient:

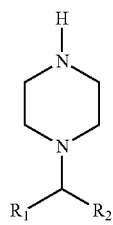

[Formula 1]

wherein, in Formula 1, each of $R_1$ and $R_2$ is independently O, H, a $C_1$-$C_4$ alkyl, a $C_1$-$C_4$ carboxyl group, or a double-bonded primary amine (=NH) or a single-bonded secondary amine ($NH_2$).

The derivative of the present invention may be piperazine-1-carboxamidine represented by Formula 2 below, but the present invention is not limited thereto:

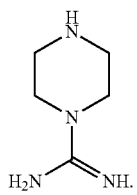

[Formula 2]

The autism spectrum disorder of the present invention may include, but is not limited to, any one or more symptoms selected from the group consisting of hyperactivity, lack of sociability, and epileptic convulsions, and may include any symptom that has been reported as symptoms of autism spectrum disorder.

Figure 1:
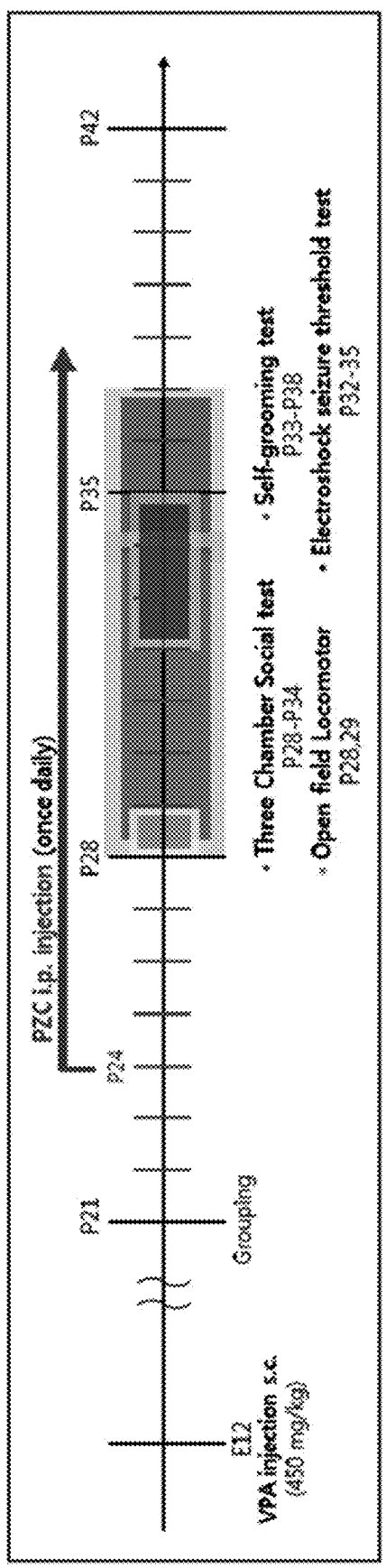
FIG. 1 is a schematic diagram illustrating the production of an autism animal model and an animal experiment to carry out the present invention.

In a specific embodiment of the present invention, the inventors of the present invention prepared babies born from pregnant rat administered valproic acid as autism animal models to be used as experimental groups (see FIG. 1).

Figure 2A:
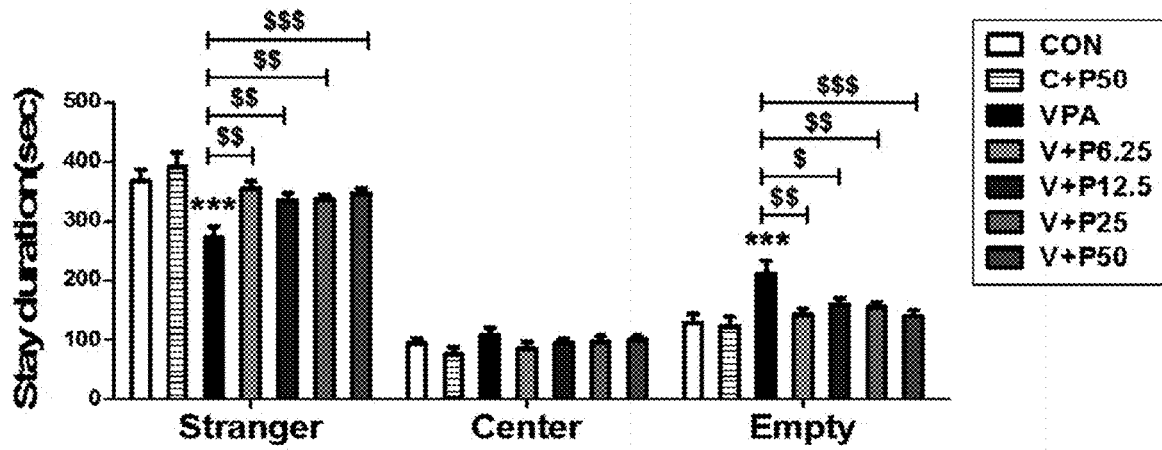
Figure 2B:
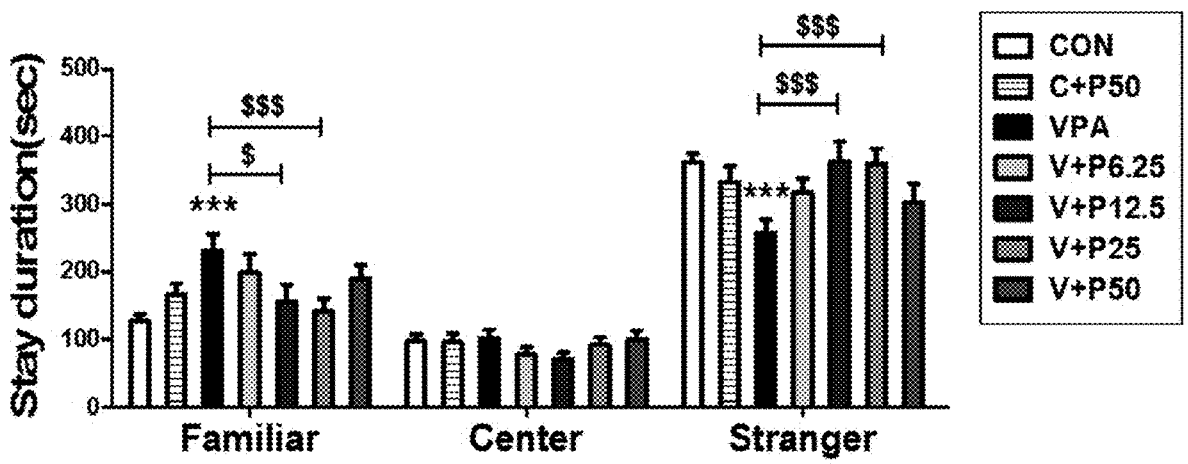

In addition, the inventors of the present invention examined changes in social interaction according to whether piperazine-1-carboxamidine was administered or not in the prepared autism animal models, and consequently confirmed that the autism animal models, which were administered piperazine-1-carboxamidine, exhibited increased levels of sociability and social preference as compared to those of a solvent control, that is, improved to levels of normal controls in experimental groups administered piperazine-1-carboxamidine at a dose of 6.25 mg/kg or more (see FIGS. 2A and 2B).

Figure 3:
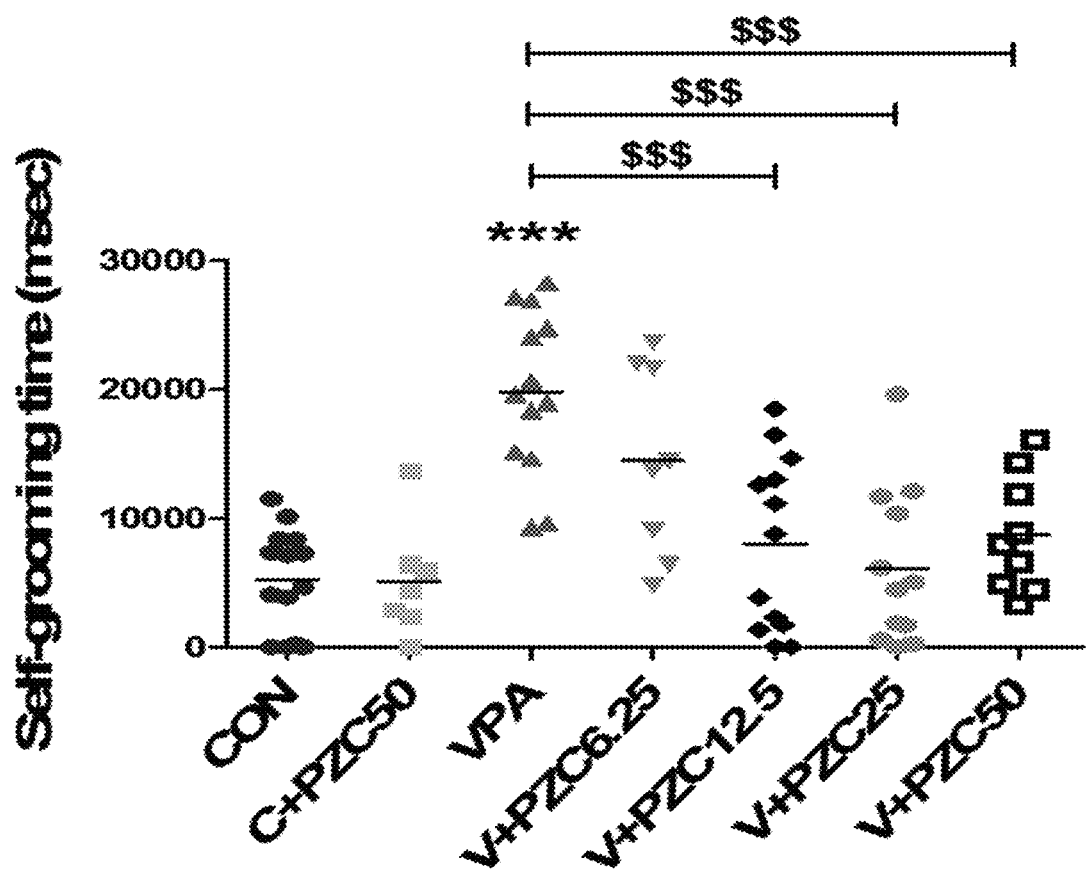
FIG. 3 illustrates an effect of piperazine-1-carboxamidine on reducing repetitive grooming behavior in autism rat models.
Figure 4A:
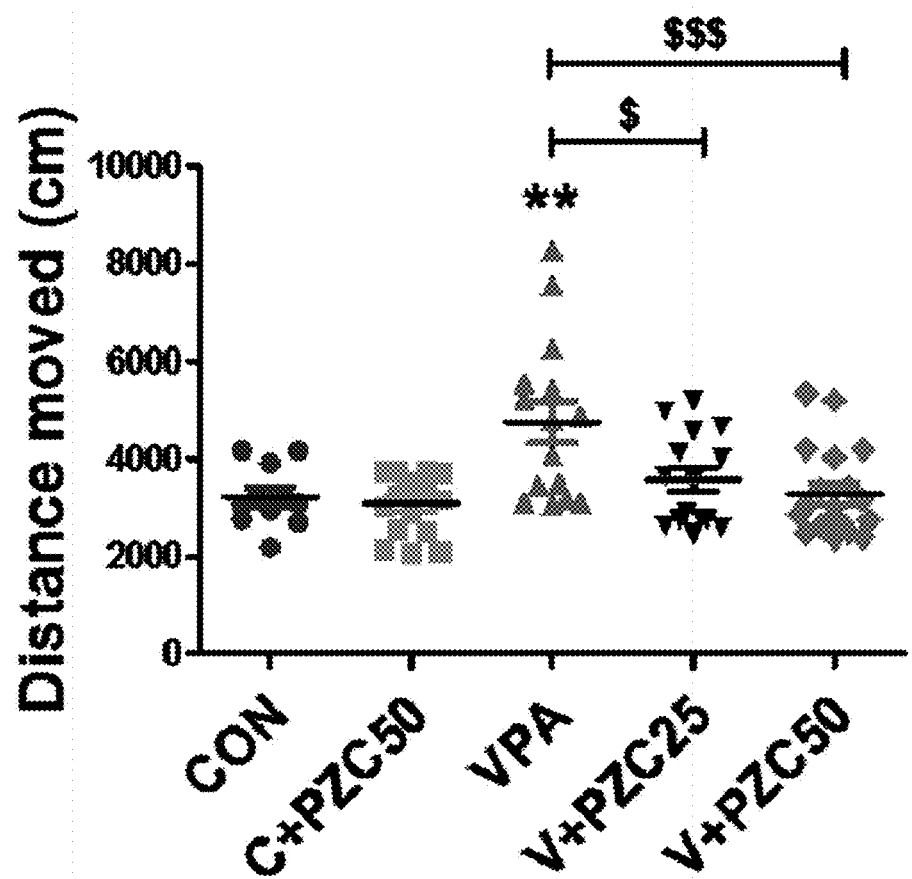
Figure 4B:
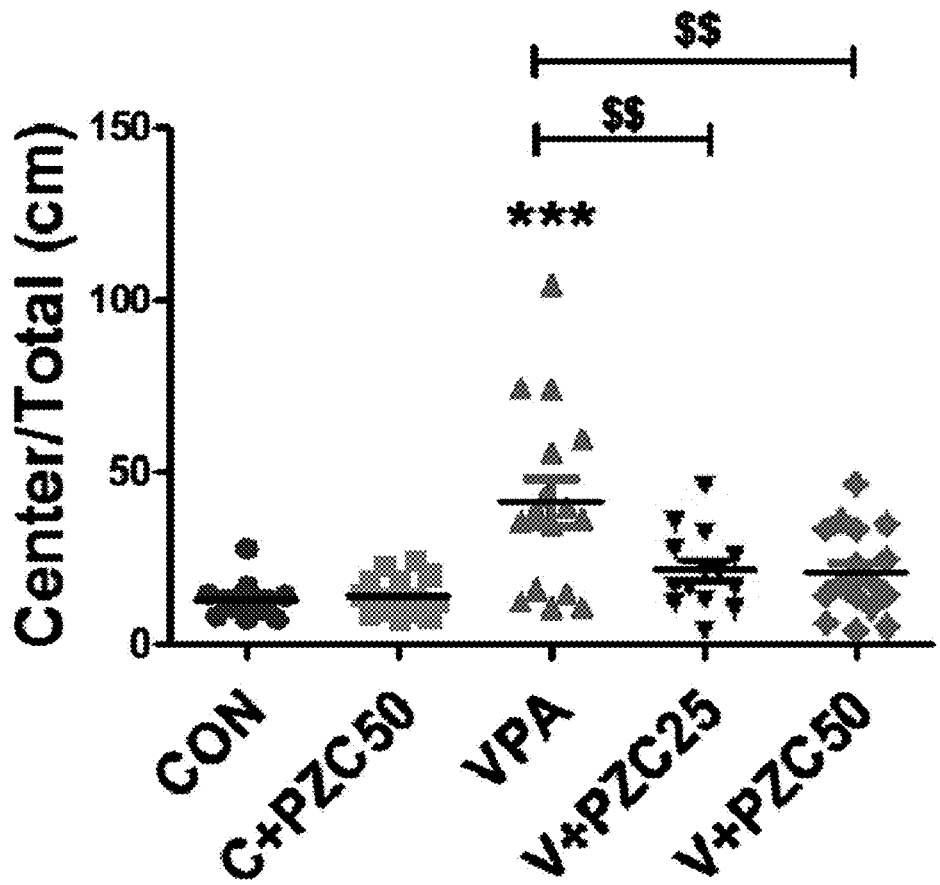

In addition, as a result of examining an effect of piperazine-1-carboxamidine on alleviating repetitive and impulsive behavioral symptoms of autism spectrum disorder, the inventors of the present invention confirmed that, when autism spectrum models were administered piperazine-1-carboxamidine, repetitive grooming behaviors were reduced (see FIG. 3), and levels of hyperactivity- and emotional disturbance-related behaviors were reduced, that is, restored to levels of normal controls (see FIGS. 4A and 4B).

Figure 5:
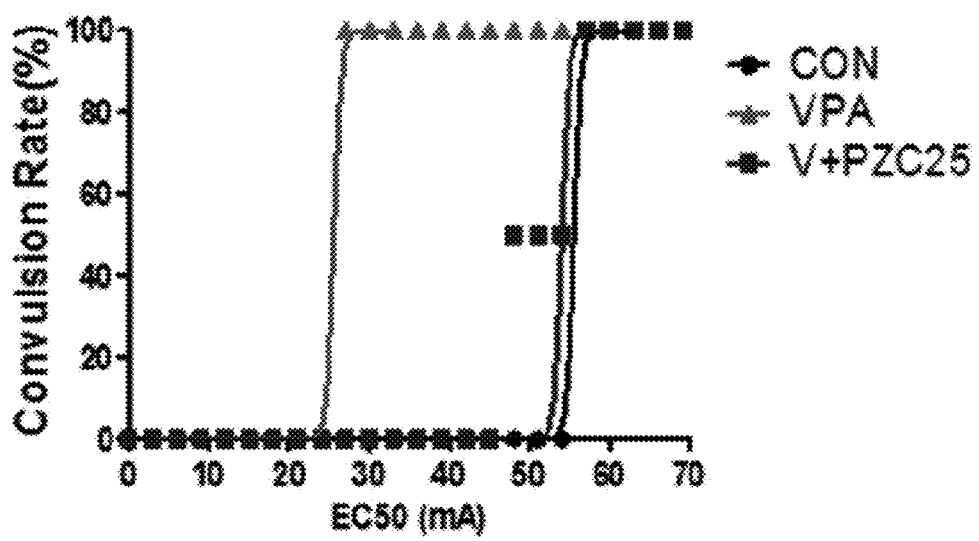
FIG. 5 illustrates changes in an electroshock-induced seizure threshold according to administration of piperazine-1-carboxamidine in autism rat models.

In addition, as a result of examining an effect of piperazine-1-carboxamidine on restoring epileptic convulsions of autism spectrum disorder, the inventors of the present invention confirmed that, when autism rat models were administered piperazine-1-carboxamidine, electroshock-induced seizure threshold values were significantly increased, as compared to a solvent control (see FIG. 5).

Accordingly, the piperazine-1-carboxamidine of the present invention exhibits, in valproic acid-induced autism rat models, an effect of improving the degrees of social interaction and social preference, reducing repetitive or restricted behaviors, hyperactivity, and impulsive behaviors, and also enhancing electroshock-induced seizure threshold susceptibility, and thus the piperazine-1-carboxamidine of the present invention may be used as an active ingredient of a pharmaceutical composition for the prevention or treatment of autism spectrum disorder.

The piperazine-1-carboxamidine of the present invention may be used in the form of a pharmaceutically acceptable salt, and the salt may be an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, and phosphorous acid; or non-toxic organic acids such as aliphatic mono- and dicarboxylates, phenyl-substituted alkanoates, hydroxy alkanoates and alkandioates, aromatic acids, and aliphatic and aromatic sulfonic acids. Examples of these pharmaceutically nontoxic salts include sulfates, pyrosulfates, bisulfates, sulfites, bisulfites, nitrates, phosphates, monohydrogen phosphates, dihydrogen phosphates, methaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butine-1,4-dioates, hexane-1,6-dioates, benzoates, chlorobenzoates, methylbenzoates, dinitro benzoates, hydroxybenzoates, methoxybenzoates, phthalates, terephthalates, benzene sulfonates, toluene sulfonates, chlorobenzene sulfonates, xylenesulfonates, phenyl acetates, phenylpropionates, phenylbutyrates, citrates, lactates, β-hydroxybutyrates, glycolates, maleates, tartrates, methanesulfonates, propanesulfonates, naphthalene-1-sulfonates, naphthalene-2-sulfonates, and mandelates.

Acid addition salts according to the present invention may be prepared using a conventional method, for example, by dissolving piperazine-1-carboxamidine in an excess of an aqueous acid solution and precipitating the salt using a water-miscible organic solvent, e.g., methanol, ethanol, acetone, or acetonitrile, or may also be prepared by heating the same amount of piperazine-1-carboxamidine and an acid or alcohol in water, and then evaporating and drying the resulting mixture or suction-filtering the precipitated salt.

In addition, pharmaceutically acceptable metallic salts may be prepared by using bases. Alkali metal or alkaline earth metal salts are obtained by, for example, dissolving a compound in an excess of an alkali metal hydroxide or alkaline earth metal hydroxide solution, filtering a non-soluble compound salt, and evaporating and drying the filtrate. At this time, it is pharmaceutically preferable that a sodium salt, a potassium salt, or a calcium salt is prepared as a metal salt. In addition, silver salts corresponding thereto are obtained by reacting an alkali metal or an alkaline earth metal salt with a suitable silver salt (e.g., silver nitrate).

Moreover, the piperazine-1-carboxamidine of the present invention includes not only pharmaceutically acceptable salts thereof, but also all salts, hydrates, and solvates that may be prepared using general methods.

Addition salts according to the present invention may be prepared using general methods, for example, by dissolving piperazine-1-carboxamidine in a water-miscible organic solvent, e.g., acetone, methanol, ethanol, acetonitrile, or the like, adding an excess of an organic acid or an aqueous inorganic acid solution thereto, and then precipitating or crystallizing the resulting solution. Subsequently, the solvent or the excess of the acid may be evaporated from the mixture, followed by drying, thereby obtaining an addition salt, or the precipitated salt may be subjected to suction filtration.

In a case in which the composition of the present invention is used as a drug, the pharmaceutical composition including piperazine-1-carboxamidine or a pharmaceutically acceptable salt thereof as an active ingredient may be formulated into various dosage forms for oral or parenteral administration in clinical trials, which will be provided below, and administered, but the present invention is not limited thereto.

Examples of preparations for oral administration include tablets, pills, hard/soft capsules, liquids, suspensions, emulsions, syrups, granules, elixirs, and the like. These preparations include, in addition to the active ingredient, a diluent (e.g., lactose, dextrose, sucrose, mannitol, sorbitol, cellulose, and/or glycine), and a lubricant (e.g., silica, talc, stearic acid and magnesium or calcium salts thereof, and/or polyethylene glycol). Tablets may include a binder such as magnesium aluminum silicate, starch paste, gelatin, methyl cellulose, sodium carboxymethylcellulose, and/or polyvinyl pyrrolidone, and in some cases, may include a disintegrating agent such as starch, agar, alginic acid or sodium salts thereof, or boiling mixture and/or an absorbent, a coloring agent, a flavoring agent, and a sweetening agent.

The pharmaceutical composition including piperazine-1-carboxamidine or a pharmaceutically acceptable salt thereof as an active ingredient, according to the present invention may be administered parenterally, and parenteral administration is performed via subcutaneous injection, intravenous injection, intramuscular injection, or intrathoracic injection. In this regard, to formulate preparations for parenteral administration, the pharmaceutical composition including piperazine-1-carboxamidine or a pharmaceutically acceptable salt thereof as an active ingredient may be mixed with a stabilizer or a buffer in water to prepare a solution or a suspension, followed by preparation into an ampoule or vial unit dosage form. The composition may be sterilized and/or include an adjuvant such as a preservative, a stabilizer, wettable powder, an emulsifying agent, a salt for the control of osmotic pressure, and/or a buffer, and other therapeutically effective materials, and may be formulated using a conventional method, such as mixing, granulation, or coating.

In addition, a dose of the composition of the present invention, which is to be administered to the human body, may vary depending on the age, body weight, and gender of patients, administration forms, health conditions, and the severity of diseases, and may generally range from 0.001 mg/day to 1,000 mg/day, preferably 0.01 mg/day to 500 mg/day, with respect to an adult patient with a body weight of 60 kg, and the composition of the present invention may also be administered once a day or in multiple doses at regular intervals in accordance with the prescription of a doctor or a pharmacist.

The present invention also provides a health functional food for the prevention or treatment of autism spectrum disorder, which includes a derivative represented by Formula 1 below or a pharmaceutically acceptable salt thereof as an active ingredient:

[Formula 1]

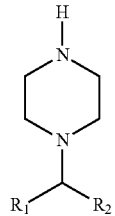

wherein, in Formula 1, each of $R_1$ and $R_2$ is independently O, H, a $C_1$-$C_4$ alkyl, a $C_1$-$C_4$ carboxyl group, or a double-bonded primary amine (=NH) or a single-bonded secondary amine ($NH_2$).

The derivative of the present invention may be, but is not limited to, piperazine-1-carboxamidine represented by Formula 2 below:

[Formula 2]

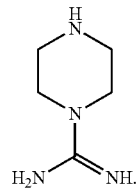

The autism spectrum disorder of the present invention may include, but is not limited to, any one or more symptoms selected from the group consisting of hyperactivity, lack of sociability, and epileptic convulsions, and may include any symptom that has been reported as symptoms of autism spectrum disorder.

Thus, the piperazine-1-carboxamidine of the present invention exhibits, in valproic acid-induced autism rat models, an effect of improving the degrees of social interaction and social preference, reducing repetitive or restricted behaviors, hyperactivity, and impulsive behaviors, and also enhancing electroshock-induced seizure threshold susceptibility, and thus the piperazine-1-carboxamidine of the present invention may be used as an active ingredient of a health functional food for the prevention or treatment of autism spectrum disorder.

The piperazine-1-carboxamidine of the present invention or a pharmaceutically acceptable salt thereof may be added directly or in combination with other foods or food ingredients, and may be appropriately used using a general method. The health functional food of the present invention includes ingredients commonly added in food preparation, for example, proteins, carbohydrates, fats, nutrients, and seasoning agents.

The type of the food is not particularly limited. Examples of foods to which piperazine-1-carboxamidine may be added include drinks, meats, sausages, bread, biscuits, rice cakes, chocolates, candies, snacks, confectionaries, pizzas, instant noodles, other noodles, gums, dairy products including ice creams, various kinds of soup, beverages, alcoholic drinks, vitamin complexes, dairy products, processed dairy products, and the like, and all health functional foods in the ordinary sense are included.

The piperazine-1-carboxamidine of the present invention or a pharmaceutically acceptable salt thereof may be added to a food directly or in combination with other foods or food ingredients, and may be appropriately used using a general method. The amount of the active ingredient to be mixed may be appropriately determined according to the purpose of use (for prevention or treatment). Generally, the amount of the compound in the health functional food may range from 0.1 part by weight to 90 parts by weight with respect to a total weight of the food. However, in the case of long-term ingestion for health and hygienic purposes or for health control purposes, the amount may be the above range or less, and since there is no problem in terms of safety, the active ingredient may also be used in an amount within the above range or greater than that.

A health functional beverage composition of the present invention may include the compound of the present invention as an essential ingredient at the indicated ratio, and other ingredients thereof are not particularly limited, and the health functional beverage composition may include additional ingredients such as various flavoring agents, natural carbohydrates, or the like as in general beverages. Examples of the above-described natural carbohydrates include general sugars such as monosaccharides, e.g., glucose, fructose, and the like; disaccharides, e.g., maltose, sucrose, and the like; and polysaccharides such as dextrin, cyclodextrin, and the like, and sugar alcohols such as xylitol, sorbitol, erythritol, and the like. As a flavoring agent other than the above-described flavoring agents, a natural flavoring agent (thaumatin and stevia extracts (e.g., rebaudioside A, glycyrrhizin, and the like) and a synthetic flavoring agent (saccharin, aspartame, and the like) are preferably used. The proportion of the natural carbohydrates generally ranges from about 1 g to about 20 g, preferably about 5 g to about 12 g, with respect to 100 g of the composition of the present invention.

In addition to the above-listed ingredients, the piperazine-1-carboxamidine of the present invention or a pharmaceutically acceptable salt thereof may include various nutritional supplements, vitamins, minerals (electrolytes), flavors such as synthetic flavors, natural flavors, and the like, colorants and enhancers (cheese, chocolates, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. In addition, the piperazine-1-carboxamidine of the present invention or a pharmaceutically acceptable salt thereof may include flesh for the preparation of natural fruit juice, fruit juice beverages, and vegetable beverages. These ingredients may be used alone or a combination thereof may be used. The proportion of these additives is not very important, but the amounts of the additives generally range from about 0.1 part by weight to about 20 parts by weight with respect to 100 parts by weight of the piperazine-1-carboxamidine of the present invention or a pharmaceutically acceptable salt thereof.

Hereinafter, the present invention will be described in further detail with reference to the following examples. It will be obvious to those of ordinary skill in the art that these examples are provided for illustrative purposes only and are not construed as limiting the scope of the present invention.

EXAMPLES

[Example 1] Preparation of Autism Animal Models

<1-1> Preparation of Valproic Acid-Induced Autism Animal Models (Valproic Acid Models)

Genetic and environmental models may be used as models for studying autism spectrum disorder. Among them, valproic acid is known to increase the probability of developing autism spectrum disorder by about 20 times that of normal mothers, when pregnant rat were exposed thereto, and in some studies on causes of autism spectrum disorder, it is known that patients with autism spectrum disorder induced by valproic acid are about 8.9%, and thus autism rat models were prepared using valproic acid to be used as subjects in the present invention.

In particular, valproic acid was subcutaneously injected into female adult Sprague-Dawley (SD) rats on day 12 of gestation, at a dose of 450 mg/kg and in an administration amount of 10 ml/kg, and then the SD rats gave birth to babies. When the born babies were 21 days old, they were grouped according to body weight and selected as autism rat models. As a group administered a solvent, on day 12 of gestation, female adult SD rats were administered a saline solution instead of valproic acid, at the same dose and in the same administration amount.

<1-2> Administration of Piperazine-1-Carboxamidine

As experimental groups for verifying an autism spectrum disorder therapeutic effect in the present invention, autism rat models were administered piperazine-1-carboxamidine.

The autism rat models prepared according to Example <1-1> were intraperitoneally administered piperazine-1-carboxamidine 24 days after birth once a day at a predetermined time. At this time, piperazine-1-carboxamidine was administered at a dose of 6.125 mg/kg, 12.5 mg/kg, 25 mg/kg, or 50 mg/kg, and in an amount of 10 ml/kg. The administration process was repeated until all the experiments were completed, and was performed 30 minutes before experiments, in the case of behavioral experiments.

[Example 2] Social Interaction Test for Piperazine-1-Carboxamidine with Respect to Autism Spectrum Disorder <2-1> Verification of Effect of Piperazine-1-Carboxamidine on Enhancing Social Interaction in Autism Rat Models To verify an effect of piperazine-1-carboxamidine on treating autism spectrum disorder in valproic acid-induced autism rat models, changes in social interaction according to whether piperazine-1-carboxamidine was administered or not were examined (Crawley, Jacqueline N. Mental retardation and developmental disabilities research reviews 10.4 (2004): 248-258).

In particular, in a transparent box structure divided into three compartments, a round cage made of a wire mesh was placed in the opposite compartments, the autism rat models aged between 28 days and 34 days, which had been repeatedly administered piperazine-1-carboxamidine in Example <1-2>, were placed in the middle compartment, followed by a social experiment for 10 minutes. Conditions and the number of individuals of experimental groups and controls are the same as shown in Table 1 below. The same kind of rats were placed in one of the opposite cages and the other thereof was left empty, and interest expressed by the autism rat models as experimental groups in the same kind of rats and social interest expressed thereby in a cage, which is a new object, were confirmed using the EthoVision system (Noldus IT b.v., Netherlands) by measuring residence time for each case. A significance test was performed using two-way ANOVA, followed by a Bonferroni's post hoc test.

TABLE 1

Autism rat model experimental groups and controls for social interaction test

| Classification | Denoted as | Number of individuals | Presence or absence of autism induction (presence or absence of exposure to valproic acid) | Amount of administered piperazine-1-carboxamidine (mg/kg) |
|---|---|---|---|---|
| Normal control 1 | con | 14 | x | 0 |
| Normal control 2 | C + P50 | 9 | x | 50 |
| Solvent control | VPA | 11 | o | 0 |
| Experimental group | V + P 6.25 | 7 | o | 6.25 |
| | V + P12.5 | 12 | o | 12.5 |
| | V + P25 | 14 | o | 25 |
| | V + P50 | 15 | o | 50 |

As a result, as illustrated in FIG. 2A, it was confirmed that the autism rat model, which is a solvent control, exhibited low interest in new rat (strangers) as compared to non-administered control rat. It was confirmed in the experimental groups administered piperazine-1-carboxamidine that the degree of interest in new rat was significantly increased in the experimental groups administered piperazine-1-carboxamidine at a dose of 6.25 mg/kg or more as compared to the solvent control, and sociability was increased in the autism rat models according to administration of piperazine-1-carboxamidine (see FIG. 2A). It was confirmed that the degree of interest in the new empty side was decreased in the experimental groups administered piperazine-1-carboxamidine at a dose of 6.25 mg/kg or more as compared to the solvent control, thus exhibiting increased sociability.

<2-2> Verification of Effect of Piperazine-1-Carboxamidine on Enhancing Social Preference in Autism Spectrum Disorder Rat Models To further verify an effect of piperazine-1-carboxamidine on treating autism spectrum disorder in valproic acid-induced autism rat models, an experiment for confirming social preference was carried out.

In particular, after social interest was confirmed in Example <2-1>, another identical type of rat were placed in the empty cage at one end of the box structure, and a social interaction experiment for the autism rat models as experimental groups was conducted for 10 minutes. Conditions and the number of individuals of experimental groups and controls are the same as shown in Table 2 below. The cage in which rat were placed in Example <2-1> was regarded as a familiar side, the cage in which new rat were placed was regarded as a novel side, and the degree of interest expressed by the autism rat models as experimental groups was confirmed using the EthoVision system by measuring residence time for each case. A significance test was performed using two-way ANOVA, followed by a Bonferroni's post hoc test.

TABLE 2

Autism rat model experimental groups and controls for confirming the degree of social preference

| Classification | Denoted as | Number of individuals | Presence or absence of autism induction (presence or absence of exposure to valproic acid) | Amount of administered piperazine-1-carboxamidine (mg/kg) |
|---|---|---|---|---|
| Normal control 1 | con | 14 | x | 0 |
| Normal control 2 | C + P50 | 9 | x | 50 |
| Solvent control | VPA | 13 | o | 0 |
| Experimental group | V + P 6.25 | 8 | o | 6.25 |
| | V + P12.5 | 10 | o | 12.5 |
| | V + P25 | 12 | o | 25 |
| | V + P50 | 16 | o | 50 |

As a result, as illustrated in FIG. 2B, it was confirmed that the autism-induced solvent control exhibited a high level of interest in the familiar side and a low level of interest in the novel side as compared to those of the normal controls, whereas the experimental groups administered 12.5 mg/kg or 25 mg/kg of piperazine-1-carboxamidine exhibited an decreased level of interest in the familiar side and an increased level of interest in the novel side, and exhibited social preference patterns restored to levels similar to those of the normal controls (see FIG. 2B).

[Example 3] Verification of Repetitive or Restricted Behavior (Marble Burying Test) Enhancement Effect of Piperazine-1-Carboxamidine on Autism Spectrum Disorder It is known that rat generally exhibit grooming by decorating their bodies, but autism rat models excessively exhibit grooming, and in severe cases, it causes hair loss and body wounds (McFarlane, H. G., et al. Genes, Brain and Behavior 7.2 2008: 152-163). To confirm an autism therapeutic effect of piperazine-1-carboxamidine in valproic acid-induced autism rat models based on these findings, a grooming level enhancement effect was evaluated in the autism rat models.

In particular, the autism rat models of Example <1-2>, which were administered piperazine-1-carboxamidine and aged between 33 days and 38 days, were placed in a cage (42 cm×29 cm×19 cm) without straw litter and adapted thereto for 10 minutes. Thereafter, the grooming time of the autism rat models was measured for 10 minutes to confirm the degree of repetitive behavior. Conditions and the number of individuals of experimental groups and controls are the same as shown in Table 3 below. A significance test was performed using one-way ANOVA, followed by a Bonferroni's post hoc test.

TABLE 3

Autism rat model experimental groups and controls of for marble burying test

| Classification | Denoted as | Number of individuals | Presence or absence of autism induction (presence or absence of exposure to valproic acid) | Amount of administered piperazine-1-carboxamidine (mg/kg) |
|---|---|---|---|---|
| Normal control 1 | con | 12 | x | 0 |
| Normal control 2 | C + PZC50 | 7 | x | 50 |
| Solvent control | VPA | 13 | o | 0 |
| Experimental group | C + PZC6.25 | 8 | o | 6.25 |
| | C + PZC12.5 | 13 | o | 12.5 |
| | C + PZC25 | 12 | o | 25 |
| | C + PZC250 | 9 | o | 50 |

As a result, as illustrated in FIG. 3, it was confirmed that, as compared to the autism-induced solvent control exhibiting repetitive and continuous grooming behaviors, the experimental groups administered 12.5 mg/kg or more of piperazine-1-carboxamidine exhibited a decreased degree of grooming and a restored grooming repetition level similar to that of the normal controls (see FIG. 3).

[Example 4] Verification of Hyperactivity and Impulsive Behavior Enhancement Effects of Piperazine-1-Carboxamidine on Autism Spectrum Disorder To confirm an effect of piperazine-1-carboxamidine on treating autism spectrum disorder in autism rat models, general locomotor activity of the autism rat models was evaluated by an open field test for assaying enhancement and deterioration of motor functions, sedation, excitement, anxiety, depression, the degree of avoidance, and toxicity. The open field test is a method used to measure how much motor activity experimental animal models are capable of exhibiting in a box having a certain size, and is used as an experimental method capable of determining the degree of hyperactivity disorders (Kim, Ji-Woon, et al. PloS one 9.8, 2014: e104927).

In particular, the autism rat models of Example <1-2>, which were administered piperazine-1-carboxamidine and aged 29 days and 30 days, were placed in a test box (40 cm×40 cm×30 cm) separately having a central region with an area of 15 cm×15 cm at the center thereof and behavioral patterns thereof were examined using the EthoVision system for 10 minutes. When values confirmed by the EthoVision system were analyzed, hyperactivity was determined using a total moving distance, and a ratio of a moving distance in the central region to the total moving distance was calculated to determine the degree of anxiety or impulsive behavior. Conditions and the number of individuals of experimental groups and controls are the same as shown in Table 4 below. A significance test was performed using one-way ANOVA, followed by a Bonferroni's post hoc test.

TABLE 4

Autism rat model experimental groups and controls of for open field test

| Classification | Denoted as | Number of individuals | Presence or absence of autism induction (presence or absence of exposure to valproic acid) | Amount of administered piperazine-1-carboxamidine (mg/kg) |
|---|---|---|---|---|
| Normal control 1 | con | 14 | x | 0 |
| Normal control 2 | C + PZC25 | 11 | x | 50 |
| Solvent control | VPA | 19 | o | 0 |
| Experimental group | V + PZC25 | 15 | o | 25 |
| | V + PZC50 | | o | 50 |

As a result, as illustrated in FIG. 4, it was confirmed that the autism-induced solvent control exhibited hyperactivity- and emotional disturbance-related behaviors, whereas the experimental groups administered piperazine-1-carboxamidine exhibited a significantly decreased degree of hyperactivity in the test box, that is, restored to the levels of the normal controls (see FIG. 4A). In addition, emotional disturbance-related movement in the central region was also reduced to levels of the normal controls in the experimental groups administered piperazine-1-carboxamidine, from which it was confirmed that the administration of piperazine-1-carboxamidine could improve an anti-anxiety effect in experimental models with impulsive disorders (see FIG. 4B).

[Example 5] Verification of Electroshock-Induced Seizure Threshold Susceptibility Improvement Effect of Piperazine-1-Carboxamidine on Autism Spectrum Disorder To confirm an effect of piperazine-1-carboxamidine on treating autism spectrum disorder in autism rat models, electroshock-induced seizure susceptibility was evaluated in autism rat models (Park, Hyung Geun, et al. European journal of pharmacology 574.2, 2007: 112-119; Browning, R. A., et al. Epilepsy research 6.1, 1990: 1-11).

In particular, metal clips of ECT UNIT 7801 (UGO BASILE, Italy), which is a constant current generator, were respectively put on both ears of each of the autism rat models of Example <1-2> above, which were administered 25 mg/kg of piperazine-1-carboxamidine and aged between 32 days and 35 days to apply electroshock thereto. Thereafter, electroshock was applied to induce a convulsive current of 50 mA, and it was examined whether or not the rat exhibited electroshock-induced overt hindlimb extension. When seizures occurred by electroshock at 50 mA, the degree of electroshock at which seizures did not occur was determined by repeatedly reducing electroshock by 3 mA, and in the case of no occurrence of seizures, the degree of electroshock at which seizures started to occur was determined by repeatedly increasing electroshock by 3 mA, thereby confirming an electroshock-induced seizure threshold. Convulsive current 50 (CC50), which is a threshold stimulation value at which 50% of the rat of each experimental group and the control started to exhibit seizures, was calculated using the Litchfield-Wilcoxon method. A rat group which was not administered piperazine-1-carboxamidine, in which autism was not induced, was used as a normal control (CON), and a valproic acid-induced autism rat model which was not administered piperazine-1-carboxamidine was used as a solvent control (VPA).

As a result, as illustrated in FIG. 5, it was confirmed that the autism rat model which was exposed to valproic acid exhibited a CC50 value corresponding to half of that of the normal control, whereas the CC50 value was significantly increased in the experimental group administered piperazine-1-carboxamidine (see FIG. 5).

The invention claimed is:

1. A method of treating autism spectrum disorder or a symptom of autism spectrum disorder, the method comprising administering a composition comprising an effective amount of a piperazine-1-carboxamidine represented by Formula 2 below or a pharmaceutically acceptable salt thereof to a subject diagnosed with autism spectrum disorder:

[Formula 2]

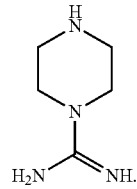

2. The method of claim 1, wherein the composition is a pharmaceutical composition.

3. The method of claim 1, wherein the composition is parenterally administered to the to the subject diagnosed with autism spectrum disorder.

4. The method of claim 1, wherein the composition is orally administered to the to the subject diagnosed with autism spectrum disorder.

5. The method of claim 1, wherein the composition is a health functional food and wherein the health functional food is ingested.

6. The method of claim 1, wherein the symptom comprises any one or more symptoms selected from lack of sociability or epileptic convulsions.

* * * * *